(12) United States Patent
Iba et al.

(10) Patent No.: US 6,479,734 B2
(45) Date of Patent: *Nov. 12, 2002

(54) DNA FRAGMENT RESPONSIVE TO LOW TEMPERATURES AND A PLANT TRANSFORMED WITH THE DNA FRAGMENT

(75) Inventors: Koh Iba, Fukuoka (JP); Takiko Shimada, Ishikawa-Gun (JP); Tomonobu Kusano, Ikoma (JP)

(73) Assignee: Kyushu University, Fukuoka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/192,434

(22) Filed: Nov. 16, 1998

(65) Prior Publication Data

US 2002/0108139 A1 Aug. 8, 2002

(30) Foreign Application Priority Data

Jun. 10, 1998 (JP) ............................................. 10-162186

(51) Int. Cl.⁷ .......................... A01H 5/00; C12N 15/29; C12N 15/82
(52) U.S. Cl. ....................... 800/298; 800/287; 735/419; 536/24.1
(58) Field of Search ................................ 800/289, 287; 536/23.6, 24.1; 435/419

(56) References Cited

U.S. PATENT DOCUMENTS 5,847,102 A * 12/1998 Singh et al.
5,929,305 A * 7/1999 Thomashow et al.

OTHER PUBLICATIONS

Maiti et al. Promoter/leader deletion analysis and plant expression vectors with the figwort mosaic virus (FMV) full length transcript (FLt) promoter containing single or double enhancer domains Transgenic Research 6. 143–156 1997.*
Donald et al. Mutation of either G box or I box sequences profoundly affects expression from the arabidopsis rbcS–1A promotor EMBO journal vol. 9 No. 6 pp. 1717–1726, 1990.*
Russell, P.J., 1998. Genetics, 5th ed. Addison Wesley Longman, Inc. Menlo Park, CA, p. G–14.*
Kusano et al, 1998. Molecular cloning and partial characterization of a tobacco cDNA encoding a small bZIP protein. Biochim. Biophys. Acta. 1395:171–175.*
Ishitani et al, 1998. HOS1, a genetic locus involved in cold–responsive gene expression in Arabidopsis. Plant Cell 10:1151–1161.*
Kusano et al, 1995. A maize DNA–binding factor with a bZIP motif is induced by low temperature. Mol. Gen. Genet. 248:507–517.*
Aguan et al, 1993. Low–temperature–dependent expression of a rice gene encoding a protein with a leucine–zipper motif. Mol. Gen. Genet. 240:1–8.*

* cited by examiner

Primary Examiner—David T. Fox
Assistant Examiner—Anne Kubelik
(74) Attorney, Agent, or Firm—Burns Doane Swecker & Mathis LLP

(57) ABSTRACT

This invention relates to a DNA fragment comprising a base sequence (a) the base sequence referred to as nucleotide numbers 1–3794 in a sequence number 1 in a sequence list; (b) the base sequence (a) a part of which is deleted or substituted by another base sequence, or to which another base sequence is added. Further, the invention relates to a recombinant DNA and transformed plant including the above fragment. Moreover, the invention relates to fragment developing a promoter activity with a responsive property to low temperatures which comprises a base sequence (c) the base sequence referred to as nucleotide numbers 1–2797 in a sequence number 1 in a sequence list; (d) A part of the base sequence (c) developing a promoter activity with a responsive property to low temperatures; or (e) The base sequence (c) or (d) a part of which is deleted or substituted by another base sequence, or to which another base sequence is added. Further, the invention relates to a recombinant DNA and transformed plant including the above fragment.

3 Claims, 1 Drawing Sheet

DNA FRAGMENT RESPONSIVE TO LOW TEMPERATURES AND A PLANT TRANSFORMED WITH THE DNA FRAGMENT

This application claims priority under 35 U.S.C. §§119 and/or 365 to 10-162186 filed in Japan on Jun. 10, 1998; the entire content of which is hereby incorporated by reference.

BACKGROUND OF THE INVENTION

1. Field of the Invention

This invention relates to a DNA fragment, a recombinant DNA suitable to produce a breed of plant such as a maize or rice plant having a resistance to low temperatures, and a transformed plant.

2. Description of Related Art

From studies so far, it has been found that there is a significant relationship between the resistance of a plant to a low temperature and the degree of unsaturation of the fatty acids constructing a biomembrane thereof.

SUMMARY OF THE INVENTION

The inventors experimentally indicated that a transformed tobacco plant comes to have a higher resistance against low temperatures when a fatty acid unsaturating enzyme gene FAD7 derived from an arabidopsis is highly expressed in the plant.

When the production of a certain protein in a plant cell is required, a promoter operating constitutively and having a high promoter activity has been used. Such a promoter operates continuously, which is unnecessary in the plant.

For instance, a constitutive promoter is also employed when a protein, which gives a plant resistance to low temperatures, is expressed. Therefore, even at ordinary temperatures, the protein, which gives the plant resistance to low temperatures, is forced to be unnecessarily expressed, causing unfavorable results.

For such reasons, the development of a site-specific and inducible promoter has been required. Particularly, it is required that the expression of a specific gene is strengthened only at low temperatures, in order to produce a breeding intermediate mother body in which a gene expressing an enzyme for unsaturating a fatty acid and other protein genes contributing to a low temperature resistance are inducibly expressed in response to low temperatures, or in order to make possible the production of an unstable functional protein using a plant cell.

It is, therefore, an object of the invention to produce a promoter capable of strengthening the expression of a fatty-acid-unsaturating-enzyme gene and other protein genes contributing to a low temperature resistance in response to low temperatures.

Another object of the invention is to produce a breed of plant having a low temperature resistance using the above promoter.

Still another object of the invention is to utilize a promoter in an inducible system of a functional protein in a plant cell, said promoter being specific to low temperatures.

According to a first aspect of the invention, there is the provision of a DNA fragment comprising a base sequence (a) or (b) described below:

(a) The base sequence referred to as nucleotide numbers 1–3794 of SEQ ID NO;1;

(b) The base sequence (a) a part of which is deleted or substituted by another base sequence, or to which another base sequence is added.

According to an aspect of the invention, there is the provision of a recombinant DNA and a transformed plant having a low temperature resistance and said plant is transformed with said recombinant DNA.

According to a second aspect of the invention, there is the provision of a DNA fragment with a promoter activity and with a responsive property to low temperatures, which comprises a base sequence (c), (d), or (e) described below:

(c) The base sequence referred to as nucleotide numbers 1–2797 of SEQ ID NO:1;

(d) A part of the base sequence (c) with a promoter activity and with a responsive property to low temperatures;

(e) The base sequence (c) or (d), a part of which is deleted or substituted by another base sequence, or to which another base sequence is added.

According to another aspect of the invention, there is the provision of a recombinant DNA which includes the DNA fragment comprising the base sequence (c), (d), or (e) described above, and a transformed plant transformed with the recombinant DNA and which phenotypically expresses a specific protein in response to low temperatures.

According to a third aspect of the invention, there is the provision of a DNA fragment with a promoter activity, which comprises a base sequence (f), (g), or (h) described below:

(f) The base sequence referred to as nucleotide numbers 1–2271 of SEQ ID NO;1;

(g) A part of the base sequence (f) with a promoter activity;

(h) The base sequence (f) or (g) a part of which is deleted or substituted by another base sequence, or to which another base sequence is added.

According to a forth aspect of the invention, there is the provision of a DNA fragment with a responsive property to low temperatures, which comprises a base sequence (i), (j), or (k) described below:

(i) The base sequence referred to as nucleotide numbers 2272–2797 of SEQ ID NO:1;

(j) A part of the base sequence (i) with a responsive property to low temperatures;

(k) The base sequence (i) or (j), a part of which is deleted or substituted by another base sequence, or to which another base sequence is added.

Since the rice low temperature inducible gene lip19 or the maize low temperature inducible gene mlip15 codes a DNA binding factor, they are considered to be a gene controlling transcription of other gene groups induced or repressed under low temperature stress. The inventors have clarified a functional unit of a low temperature inducible promoter in the maize's mlip15 gene and have clarified that the functional unit also operates in a transformed plant.

The inventors have isolated a genomic clone of the maize's mlip15 gene by a common method. After determination of the nucleotide sequence, it became clear that the gene does not include an intron (see: Sequence number 1 in Sequence list)

In the gene mlip15, 2.8 kb of the nucleotide sequence (0.6 kb of a nontranslated region at 5'-end and 2.2 kb of a nucleotide sequence linking at upstream thereof, in a mlip15 cDNA) and 2.2 kb of the nucleotide sequence (the nucleotide sequence remained after subtracting 0.6 kb of the nontranslated region at 5'-end from the 2.8 kb of the nucleotide sequence) are respectively fused with a β-glucuronidase gene as a reporter gene to make recombinant DNAs.

Each recombinant DNA is introduced into a callus derived from a rice's scutellum by using a particle gun. The result is that the former (the 2.8 kb nucleotide sequence) maintains a reactivity for low temperatures but the latter (the 2.2 kb nucleotide sequence) loses it. Therefore, it has been clarified that the 2.8 kb fragment containing 0.6 kb of the nontranslated region at 5'-end has a promoter function responsive to low temperatures.

In the invention, as a vector used for producing a recombinant DNA, a plasmid can, for example, be employed. Further, as a plant in which to introduce the recombinant DNA, a useful cultivating monocotyledon such as maize, rice, wheat, barley, oat, Italian millet, or Japanese millet is preferably used.

A protein produced by induction of the promoter according to the invention includes an ω-3-fatty acid unsaturating enzyme etc.

Moreover, the invention includes a base sequence where one or several nucleotides of which are deleted or substituted by another base sequence, or to which another base sequence is added, if it maintains the promoter function according to the invention.

BRIEF DESCRIPTION OF THE DRAWING

The invention will be described with reference to the accompanying drawing, wherein.

Figure 1:
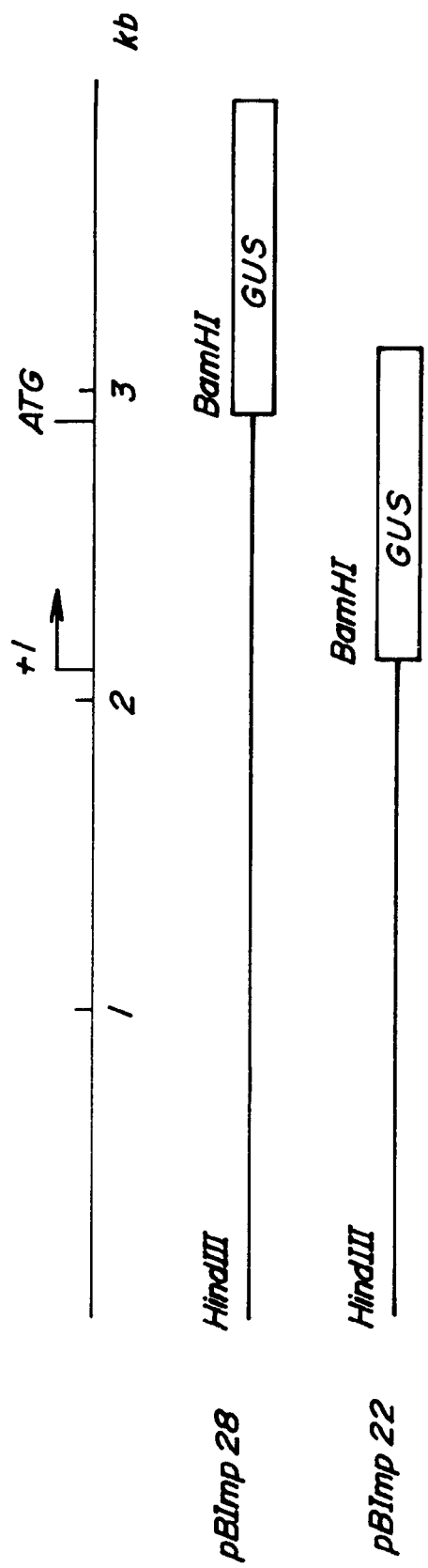
FIG. 1 is an illustration diagrammatically showing mlip15 regions.

DESCRIPTION OF THE PREFERRED EMBODIMENTS (Isolation of mlip15 genomic clone and determination of the nucleotide sequence)

A genome DNA prepared from a maize (breed: honey bantam) is cut (partially digested) by a restriction enzyme Sau3A and then separated by using a sucrose density gradient centrifugation to obtain a 9.7–22 kb DNA fraction. The DNA fraction is fused with a λ-EMBL3 digested by BamHI and then phage particles are made by using GigapackGoldIIkit.

By using *Escherichia coli* XL1-Blue MRA (P2) as a host, 1×10$^7$ pfu/ml of a library is obtained.

The library is selected by using the whole length of the mlip15 cDNA as a probe to obtain three positive clones.

Among them, a clone named "λH1" is found to include 11.5 kb of a fragment containing the mlip15 cDNA, 5 kb of a fragment at the 5'-end, upstream thereof, and 5 kb of fragment at the 3'-end, downstream thereof.

In SEQ ID NO:1 there is shown 3,794 bp of a nucleotide sequence being an EcoRI-BamHI fragment including (consisting of) the whole length of the mlip15 cDNA.

A putative amino acid sequence at the region coding an mlip15 protein is symbolized under the base sequence by one capital letter. Nucleotide numbers corresponding to the assumed amino acid sequence are 2798–3205. A terminal codon of the base sequence is shown as a mark "*". A nucleotide sequence which is assumed as the "TATA box" is underlined and also has a description of "TATA box" thereunder. A transcription initiation point of mlip15 is T as nucleotide number 2272.

(Constructing of recombinant DNA used for introducing into rice's callus).

A fragment having the nucleotide numbers 1–2797 and a fragment having the nucleotide numbers 1–2271 are respectively amplified by a PCR method (a polymerase chain reaction method) using the maize'mlip15 genomic clone as a template. The fragment of nucleotide numbers 1–2797 corresponds to the above mentioned 2.8 kb genomic sequence, which consists of 0.6 kb of a nontranslated region at the 5'-end and 2.2 kb of genomic sequences upstream of the 0.6 kb 5'-nontranslated region of the mlip15 cDNA. The fragment of nucleotide numbers 1–2271 corresponds the above mentioned 2.2 kb genomic sequence, which consists of the 2.8 kb nucleotide sequence minus the 0.6 kb 5'-nontranslated region.

Nucleotide numbers 2798–3205 correspond to the coding region of the mlip15 protein.

LATaqDNA polymerase, which has a proofreading activity, is used as an enzyme in the above described PCR reactions. In this case, each primer is such designed that the base sequence of the nucleotide numbers 1–6 becomes a Hind III site (AAGCTT) and the base sequence of the nucleotide numbers 2792–2797 and the base sequence of the nucleotide numbers 2266–2271 respectively become a Bam HI site (GGATCC).

Each amplified fragment is integrated between the Bam HI and Hind III sites of a pUC18 vector and a confirmation of each base sequence is conducted. Using each plasmid with each base sequence confirmed, each Bam HI–Hind III fragment respectively consisting of 2797 bp and 2271 bp is reproduced and integrated between the Bam HI and Hind III sites of pBI 221. Each obtained recombinant plasmid is respectively named pBImp28 (because it contains 2.8 kb of the promoter region of mlip15) and pBImp22 (because it contains 2.2 kb of the promoter region of mlip15).

In FIG. 1, the mlip15 promoter region is diagrammatically illustrated. The mlip15 promoter portion contained in the above recombinant-plasmid is shown therein. The symbol of "+1" indicates a transcription initiation point (the nucleotide number 2272), the symbol of "key arrow" indicates the direction of transcription, and the symbol of "ATG" indicates the position of a transcription initiation codon (the nucleotide number 2798). A β-glucuronidase gene (abbreviated as GUS) is used as a reporter gene (its scale is not correct in the figure).

(Reactivity of the introduced plasmid in low temperatures).

To a callus derived from a rice' scutellum (breed: Notohikari), each plasmid described above is introduced using a particle-gun (made by BIO-RAD Co., Ltd.) After the introduction, the callus is incubated for 24 hours in a dark place at 25° C. and then divided to two homogeneous parts. After respectively incubating for another 24 hours one at 25° C. and the other at 5° C., a GUS test is performed. A GUS activity is judged as whether a low temperature reactivity is present or not, and is determined by calculating a ratio of the number of blue spots per scutellum on an X-Gluc as substrate at 5° C. to that of 25° C. (see: Table 1). The test is repeated three times on both plasmids and the results are shown in Table 1.

TABLE 1

| Induced plasmid | Responsive property to low temperatures Ratio of GUS activity (5° C./25° C.) | |
|---|---|---|
| pBImp28 | Experimental 1 | 2.7 |
| | Experimental 2 | 6.0 |
| | Experimental 3 | 4.7 |

TABLE 1-continued

| Induced plasmid | Responsive property to low temperatures Ratio of GUS activity (5° C./25° C.) | |
| --- | --- | --- |
| pBImp22 | Experimental 1 | 1.1 |
| | Experimental 2 | 0.62 |
| | Experimental 3 | 0.57 |

When the pBImp28 is introduced, a high GUS activity is obtained. But, when the pBImp22 is introduced, the GUS activity is inferior thereto. The following may be derived from these results.

(a) In aDNA fragment of nucleotide numbers 1–3794 of the maize, mlip15 gemonic clone, the promoter region relating to the low temperature responsive property exists upstream of the putative amino acid sequence coding the mlip15 protein.

(b) The fragment of nucleotide numbers 1–2797 contains the promoter region relating to the low temperature responsive property.

(c) The fragment of nucleotide numbers 1–2271 acts as a promoter, however, this fragment does not have the responsive property to low temperatures when compared to the fragment of nucleotide numbers 1–2797. The fragment of nucleotide numbers 2272–2797 has the low temperature responsive property and both fragments together relate to the expression of the promoter.

What is claimed is:

1. An isolated DNA fragment comprising nucleotides 1–2797 of SEQ ID NO:1, wherein said DNA fragment is a promoter which is induced by low temperatures.

2. A recombinant DNA comprising the DNA fragment as claimed in claim 1.

3. A transformed plant expressing a specific protein in response to low temperatures, in which the transformed plant was transformed with a recombinant DNA comprising a nucleic acid encoding said protein operably linked to the DNA fragment of claim 1.

* * * * *

SEQUENCE LISTING

```
<160> NUMBER OF SEQ ID NOS:  2

<210> SEQ ID NO 1
<211> LENGTH: 3794
<212> TYPE: DNA
<213> ORGANISM: Maize breed of honey bantam
<220> FEATURE:
<221> NAME/KEY: CDS
<222> LOCATION: (2798)..(3205)

<400> SEQUENCE: 1
gaattccgaa taacgcgccc cgcatgcaac cagatagcgg atctttcggc gctaaactca      60
gagggaagca attgccggaa gagtcggcgt gcaagaataa cataagtaga taagatttca     120
cgatctataa aaggatatct ccctagtcgg ctatataagg ctagggaggt acccaaacaa     180
aacgaatcac tctctttcac caccataacg cccactagta gactaatatg agatctcatc     240
caccgtcacc cgcgaatcat ctgtaaccca agcaaactca atacccaaca tcacacatga     300
cttagggtat tacgcattta ggcgacccga acctgtataa ttttcttgtg tttcaacgtg     360
cacctgcacg taccatcgag ttgcgattaa cgtcgccgtc ctcccaaaaa tactggtggt     420
cctcccaaaa actcgaccgg acgatagaaa tagtgtatgg ctaagtagag caaggtggcg     480
tttggtccgc ggctatgatg agaatccagt agactgaatc cacgtgctaa accaaacatc     540
actggttttg gctgcatctt ctcggattac gtgtgttgtg caaattctca taatccacgg     600
caaccagacg ggggcgcaac caattggtgt ttcttaggaa gcccccgcgt tacattggat     660
cataggatga ttcaagggtt atgattttt agctactaat tggttgtcat catggtttat     720
aggtgaagat tgttattcaa tcaaagggcg acatatccct ccgcgtttag agacttgcgt     780
gtagtgtaaa catggatgta attgtgctac ctttaataga gtcccttagc tcttcaaaaa     840
caaatcttat tatatattaa ttactagtcc atccatttta ttctaattta gtttcgaaat     900
tactaaatat agaaaataaa atagagtttt agtagcaatt atgaaaactg aaatatagtt     960
ttaatttccg tatttagtga tttaaatact aaaatataat aaaatggaga gactaaaaac    1020
tagtccctat aaaccaaaca ttctttaaat aaagccccgt ggctaggaca atgacctatt    1080
tttttctcgc aaccggaaga ataaaaaatt caccgtaact ttctttcttt cttcttttta    1140
tgcgaaagaa gatagttgca agacgaatcc agagtttatc tggaagaaga aagttcctaa    1200
tcctcctcct tccctgtaga tattatcagc aaggcaagcg tgtcacggct tcttgcttga    1260
gtaatccgct cctatttttt tttttgggag ggcgccttcc taccggcttc gcttctaaac    1320
```

-continued

```
ggtgggcaaa tttggtacga taaagaaaaa agaggaggac gagtgggagg gcacttctgg    1380
aaaaaacttt ttaatgagct ggaccaagca gctgggcaag ctgtcactag gactggacaa    1440
aatactcgtg gctcgataac tcgctcgact cggctcgtta gtagctcagc tcgactcggc    1500 tcgtttaat tttgtagcga gccaagctag cattctagct cgattctcta atgagccagc     1560
tcgggttagc tcgtgagcta gctcgcgagc caaacgagct aagccacaac acaaatttgt    1620
ctagtcattg atgtcgtctc atctctcata gtcttgtttt ctcgtagtta tgatctgtga    1680 tatgacatg tgtggatgtg ccatgtgctt aaatatttat attattgcat ggctacatgt     1740
ttgtagtgtt aaatacttaa aatataattt ttcggttata aatatattta tgtacataga    1800
tatttatatt tagttgtgtg gctcacgagc ctaacgagct ggctcgagct tcctaacgag    1860
ccgagccgag ccagctattt agctcgttag tataacgagc cgagccgagc tggctcgtta    1920
tagtaacgag ccataacgag ccgagccata acgagccaag ctggttcgat atccaccct     1980 agctgtcacc gtcgcccagt ccgcttcgtt cggtcagcgg gccccacctc atctgcattc    2040
ttccattctc gtcctccgac ctcatctgca ttttcccagc caagtagtag gtaaactagt    2100
ggcggtcccg tggccgtggc atcaggaaaa gaatatgccg tcccagccca ccatcccccc    2160
accgtcccga aattccagaa ctaccctcgg ctccagctat aaatagccgc ccccgggaga    2220
cgttcgaaac cttccccatc tccggataaa agataaggag tgtctctcct ctctttcagc    2280
taagtccctg ctccctctct ttttcttaca ttcaggtcct cgcagctcct ctcttttttc    2340
ttgtttcttt ctttcgatct gcgagccgtc caggtccagt actctccttt ccgtgaagga    2400
actcttgcag ccggcccctc tggtttcctc gaattcttgt tccccggtcc ctcctcctgt    2460
ccccgcgtag atccgtccgt ccgaggagca caccgtcccc accccatgt ttacccacca     2520 gttcctctga cggccgccgt gctccgatga agctgagcgt gctccgtatc cgccgctccc    2580
actccttctc cgtcgccttc ctctactggt tctacgtctt ctcatgaacg catcgcccct    2640
ctccacctgc tgatccttcg ccatctctcc atctctcttt ctctctgaga tagtctttcg    2700
aatccatctc tagggctctt gtttctcccc atcctccccc caccccaccc cccaccaaac    2760
acaagtcccc ttgttcaatc cgacaagaca agcatcc atg tcg tcg tca cgc cgg     2815
                                         Met Ser Ser Ser Arg Arg
                                           1               5 agc tcg agc ccc gac agc aac gac acg acg gac gag cgc aag cgg aag    2863
Ser Ser Ser Pro Asp Ser Asn Asp Thr Thr Asp Glu Arg Lys Arg Lys
           10                  15                  20 cgg atg ctg tcc aac agg gag tcg gcg cgg cgg tcg cgc gcg cgg aag    2911
Arg Met Leu Ser Asn Arg Glu Ser Ala Arg Arg Ser Arg Ala Arg Lys
       25                  30                  35 cag cag cgg ctg gag gag ctg gtg gcg gag gtg gcc cgc ctg cag gcg    2959
Gln Gln Arg Leu Glu Glu Leu Val Ala Glu Val Ala Arg Leu Gln Ala
   40                  45                  50 gag aac gcg gcg acg cag gcc cgc acc gcg gcg ctg gag cgc gac ctg    3007
Glu Asn Ala Ala Thr Gln Ala Arg Thr Ala Ala Leu Glu Arg Asp Leu
55                  60                  65                  70 ggc agg gtg gac ggc gac aac gcg gtc gtg cgc gcc cgc cac gcc gag    3055
Gly Arg Val Asp Gly Asp Asn Ala Val Val Arg Ala Arg His Ala Glu
                75                  80                  85 ctg gcc ggc cgc ctg cag tcg ctg ggc ggc gtc ctc gag gtg ctc cag    3103
Leu Ala Gly Arg Leu Gln Ser Leu Gly Gly Val Leu Glu Val Leu Gln
           90                  95                 100 atg gcc ggc gcc gcc gtc gac atc ccg gag atg gtc acc gac gac ccc    3151
Met Ala Gly Ala Ala Val Asp Ile Pro Glu Met Val Thr Asp Asp Pro
```

-continued

```
            105                 110                 115
atg ctc cgc ccc tgg cag ccg tcc ttc ccc ccg atg cag ccc atc ggg    3199
Met Leu Arg Pro Trp Gln Pro Ser Phe Pro Pro Met Gln Pro Ile Gly
        120                 125                 130 ttc tga gaatctgagc ctcagccggc gggagagagc caatttctgt cgtcgtgccg    3255
Phe
135 ctgtctatct cgtattggta tatctattca taaatcatcc ttgtcatggt ttggtcttct    3315 tgttcagtgt tataaatttg cttcttgtta gtgttataaa tttggccatc ggaaaggatg    3375 tgtttgtagt tgtaatatct tgtttggagt tgtaatatct tatcttgctt atgaaatcga    3435 atatgcctat atatatatgt tatgctgtac gagtatgtgg ctccaaattt gtgagccttc    3495 tgtctgttat ggtgaggcga tgaatccaat ttgtgagcac acatgaatca atttcgagat    3555 tcgacatgtc aagttgatcg ttgcaggaag gacggttttt gtatggacgg acataccaag    3615 ttactgcatt ttacttaaaa tatctcactt atttttttaga tcggcatttc tccactcgtt    3675 agatttcttg ttcttgagtc agaagataac tacagcatgt catatctcaa ttggaatacc    3735 attagggtcc ctcatcttaa cctatttcat ctcttttaat acgtagattt tttggatcc    3794
```

<210> SEQ ID NO 2
<211> LENGTH: 135
<212> TYPE: PRT
<213> ORGANISM: Maize breed of honey bantam

<400> SEQUENCE: 2

```
Met Ser Ser Ser Arg Arg Ser Ser Ser Pro Asp Ser Asn Asp Thr Thr
  1               5                  10                  15

Asp Glu Arg Lys Arg Lys Arg Met Leu Ser Asn Arg Glu Ser Ala Arg
                 20                  25                  30

Arg Ser Arg Ala Arg Lys Gln Gln Arg Leu Glu Glu Leu Val Ala Glu
             35                  40                  45

Val Ala Arg Leu Gln Ala Glu Asn Ala Ala Thr Gln Ala Arg Thr Ala
         50                  55                  60

Ala Leu Glu Arg Asp Leu Gly Arg Val Asp Gly Asp Asn Ala Val Val
 65                  70                  75                  80

Arg Ala Arg His Ala Glu Leu Ala Gly Arg Leu Gln Ser Leu Gly Gly
                 85                  90                  95

Val Leu Glu Val Leu Gln Met Ala Gly Ala Ala Val Asp Ile Pro Glu
            100                 105                 110

Met Val Thr Asp Asp Pro Met Leu Arg Pro Trp Gln Pro Ser Phe Pro
        115                 120                 125

Pro Met Gln Pro Ile Gly Phe
        130                 135
```